US009290455B2

(12) United States Patent
Sporn et al.

(10) Patent No.: US 9,290,455 B2
(45) Date of Patent: Mar. 22, 2016

(54) CDDO-ME AMINO ACID CONJUGATES AND METHODS OF USE

(71) Applicant: Trustees of Dartmouth College, Hanover, NH (US)

(72) Inventors: Michael B. Sporn, Tunbridge, VT (US); Karen T. Liby, West Lebanon, NH (US); Martine Cao, West Lebanon, NH (US); Evans O. Onyango, Hanover, NH (US); Liangfeng Fu, West Lebanon, NH (US); Gordon W. Gribble, Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 14/177,569

(22) Filed: Feb. 11, 2014

(65) Prior Publication Data

US 2015/0225352 A1 Aug. 13, 2015

(51) Int. Cl.
*A61K 31/21* (2006.01)
*A61K 31/275* (2006.01)
*A61K 31/40* (2006.01)
*C07D 233/61* (2006.01)
*C07C 235/84* (2006.01)
*C07D 207/16* (2006.01)
*C07D 209/08* (2006.01)

(52) U.S. Cl.
CPC ............ *C07D 233/61* (2013.01); *C07C 235/84* (2013.01); *C07D 207/16* (2013.01); *C07D 209/08* (2013.01)

(58) Field of Classification Search
CPC ............................... A61K 31/56; C07J 63/008
USPC .......................... 514/169, 170, 510, 557, 561
See application file for complete search history.

(56) References Cited

U.S. PATENT DOCUMENTS

| 6,326,507 B1 | 12/2001 | Gribble et al. ............... 558/415 |
| 6,552,075 B2 | 4/2003 | Gribble et al. ............... 514/522 |
| 6,974,801 B2 | 12/2005 | Honda et al. .................. 514/25 |
| 7,288,568 B2 | 10/2007 | Gribble et al. ............... 514/519 |
| 7,435,755 B2 | 10/2008 | Konopleva et al. ........... 514/510 |
| 7,678,830 B2 | 3/2010 | Honda et al. .................. 514/519 |
| 7,795,305 B2 | 9/2010 | Konopleva et al. ........... 514/510 |
| 7,863,327 B2 | 1/2011 | Gribble et al. ............... 514/521 |
| 8,034,955 B2 | 10/2011 | Gribble et al. ............... 548/241 |
| 8,067,394 B2 | 11/2011 | Honda et al. .................. 514/63 |
| 8,129,429 B2 | 3/2012 | Sporn et al. .................. 514/510 |
| 8,299,046 B2 | 10/2012 | Sporn et al. .................. 514/63 |
| 8,455,544 B2 | 6/2013 | Sporn et al. .................. 514/510 |
| 8,586,775 B2 * | 11/2013 | Gribble et al. ............... 558/415 |
| 8,921,340 B2 * | 12/2014 | Sporn et al. .................. 514/63 |
| 8,921,419 B2 * | 12/2014 | Gribble et al. ............... 514/510 |
| 2009/0060873 A1 | 3/2009 | Sporn et al. .................. 424/85.6 |
| 2013/0089526 A1 | 4/2013 | Sporn et al. .................. 424/93.7 |
| 2013/0122053 A1 | 5/2013 | Sporn et al. .................. 424/400 |
| 2013/0237721 A1 | 9/2013 | Gribble et al. ............... 558/429 |
| 2013/0345276 A1 | 12/2013 | Sporn et al. .................. 514/399 |

OTHER PUBLICATIONS

Dang et al. "Synthesis of Betulinic Acid Derivatives as Entry Inhibitors Against HIV-1 and Bevirimat-Resistant HIV-1 Variants" Bioorganic & Medicinal Chemistry Letters 2012 22(16):5190-5194.
Honda et al. "Design and Synthesis of 2-Cyano-3,12-Dioxoolean-1,9-Dien-28-Oic Acid, a Novel and Highly Active Inhibitor of Nitric Oxide Production in Mouse Macrophages" Bioorganic & Medicinal Chemistry Letters 1998 8:2711-2714.
Honda et al. "Novel Synthetic Oleanane and Ursane Triterpenoids with Various Enone Functionalities in Ring A as Inhibitors of Nitric Oxide Production in Mouse Macrophages" Journal of Medicinal Chemistry 2000 43:1866-1877.
Jeong et al. "Preparation of Amino Acid Conjugates of Betulinic Acid with Activity Against Human Melanoma" Bioorganic & Medicinal Chemistry Letters 1999 9:1201-1204.
Kim et al. "CDDO-Methyl Ester Delays Breast Cancer Development in *Brca1*-Mutated Mice" Cancer Prevention Research 2012 5:89-97 (published online Sep. 20, 2011).
Kress et al. "Triterpenoids Display Single Agent Anti-Tumor Activity in a Transgenic Mouse Model of Chronic Lymphocytic Leukemia and Small B Cell Lymphoma" PLOS One 2007 6:e559.
Liby, K.T. and Sporn, M.B. "Synthetic Oleanane Triterpenoids: Multifunctional Drugs with a Broad Range of Applications for Prevention and Treatment of Chronic Disease" Pharmacological Reviews 2012 64:972-1003.
Liby et al. "Synthetic Triterpenoids Prolong Survival in a Transgenic Mouse Model of Pancreatic Cancer" Cancer Prevention Research 2010 3:1427-1434.
Parra et al. "Solution- and Solid-Phase Synthesis and Anti-HIV Activity of Maslinic Acid Derivatives Containing Amino Acids and Peptides" Bioorganic & Medicinal Chemistry Letters 2009 17:1139-1145.
Sporn et al. "New Synthetic Triterpenoids: Potent Agents for Prevention and Treatment of Tissue Injury Caused by Inflammatory and Oxidative Stress" Journal of Natural Products 2011 74:537-545.
Townson et al. "The Synthetic Triterpenoid CDDO-Imidazolide Suppresses Experimental Liver Metastasis" Clinical and Experimental Metastasis 2011 28:309-317.
Tran et al. "The Synthetic Triterpenoid CDDO-Methyl Ester Delays Estrogen Receptor-Negative Mammary Carcinogenesis in Polyoma Middle T Mice" Cancer Prevention Research 2012 5:726-734.
Tran et al. "The Synthetic Triterpenoid CDDO-Methyl Ester Modulates Microglial Activities, Inhibits TNF Production, and Provides Dopaminergic Neuroprotection" Journal of Neuroinflammation 2008 5:1-14.
Zhang et al. "Synthesis and Activity of Oleanolic Acid Derivatives, a Novel Class of Inhibitors of Osteoclast Formation" Bioorganic & Medicinal Chemistry Letters 2005 15:1629-1632.

* cited by examiner

*Primary Examiner* — My-Chau T Tran
(74) *Attorney, Agent, or Firm* — Licata & Tyrrell P.C.

(57) ABSTRACT

2-Cyano-3,12-dioxooleana-1,9(11)-dien-28-oic acid amino acid derivatives having antiinflammatory properties are provided. Pharmaceutical compositions and methods for preventing or treating inflammation or a disease or condition mediated by inflammation are described.

5 Claims, 2 Drawing Sheets

CDDO-ME AMINO ACID CONJUGATES AND METHODS OF USE

BACKGROUND

Several years of design, synthetic effort, and screening of oleanolic acid (1) derivatives led to the discovery of 2-cyano-3,12-dioxooleana-1,9(11)-dien-28-oic acid (CDDO, 2) and its methyl ester, bardoxolone methyl (3) (Sporn, et al. (2011) *J. Nat. Prod.* 74:537; Honda, et al. (1998) *Med. Chem. Lett.* 8:2711), as lead compounds for further development and eventual clinical trials. Following the initial discovery of CDDO as a potent multifunctional molecule (Honda, et al. (2000) *J. Med. Chem.* 43:1866), lead compounds with enhanced activity and reduced toxicity have been identified. For example, methylation and amidation of the C-28 carboxylic acid moiety afforded CDDO-methyl ester (bardoxolone methyl) and CDDO-ethyl amide 4, respectively.

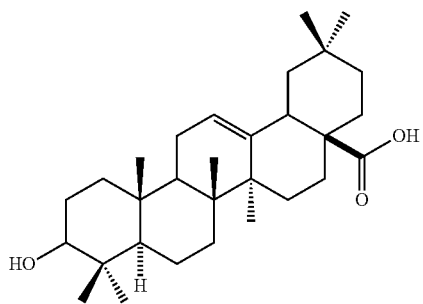

1

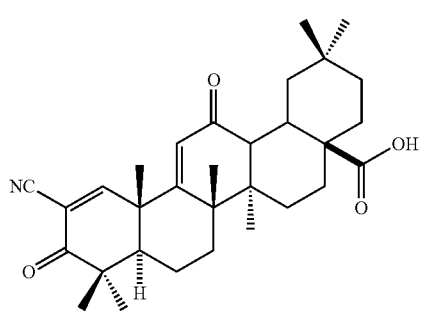

2

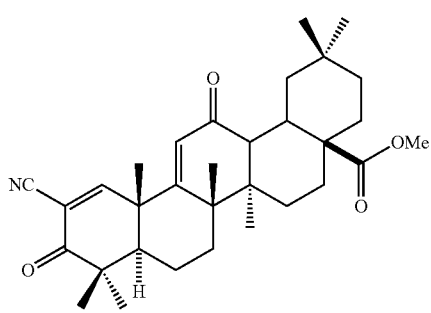

3

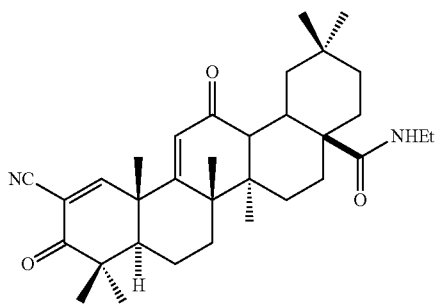

4

Synthetic triterpenoids (TP) are active at low nanomolar concentrations and inhibit the induction of iNOS (inducible nitric oxide synthase) in primary macrophages or in RAW264.7 macrophage-like cells stimulated with inflammatory cytokines. CDDO-Me (3), with significantly higher activity than that of CDDO, has advanced to clinical trials for a variety of antiinflammation disorders, including cancer and diabetic neuropathy (Liby & Sporn (2012) *Pharmacol. Rev.* 64:972). Similarly, other CDDO derivatives are known to possess antitumor activities (Tran, et al. (2008) *J. Neuroinflammation* 5:14; Liby, et al. (2010) *Cancer Prev. Res.* 3:1427; Townson, et al. (2011) *Clin. Exp. Metastasis* 28:309; Kim, et al. (2012) *Cancer Prev. Res.* 5:89; Tran, et al. (2012) *Cancer Prev. Res.* 5:726; Kress, et al. (2007) *PLoS One* 2:e559).

Oleanolic acid amino acid conjugates have been synthesized as potent inhibitors of osteoclast formation (Zhang, et al. (2005) *Bioorg. Med. Chem. Lett.* 15:1629). Furthermore, amino acid conjugates of betulinic acid exhibit potent activity against melanoma (Jeong, et al. (1999) *Bioorg. Med. Chem. Lett.* 9:1201) and HIV (Dang, et al. (2012) *Bioorg. Med. Chem. Lett.* 22:5190). The anti-HIV activity of triterpenoid maslinic acid is also enhanced by its conjugation to amino acids (Parra, et al. (2009) *Bioorg. Med. Chem.* 17:1139).

SUMMARY OF THE INVENTION

This invention is a compound of Formula I, or a pharmaceutically acceptable salt, solvate, or enantiomer thereof:

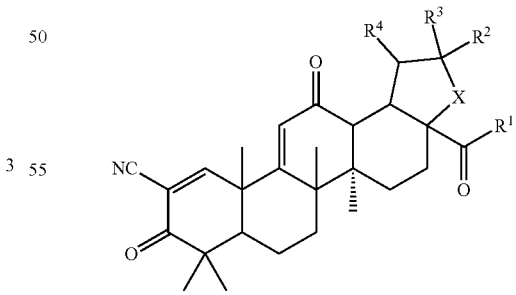

Formula I wherein $R^1$ is an amino acid group or amino acid derivative, e.g., a proteinogenic or non-proteinogenic amino acid group or amino acid derivative; $R^2$, $R^3$ and $R^4$ are each independently a hydrogen or a $C_1$-$C_3$ alkyl group and X is —$CH_2$— or —$CH_2$—$CH_2$—. A pharmaceutical composition containing the compound in admixture with a pharmaceutically acceptable carrier is also provided as is a method for preventing or treating inflammation or a disease or condition mediated by inflammation.

DETAILED DESCRIPTION OF THE INVENTION

Figure 1:
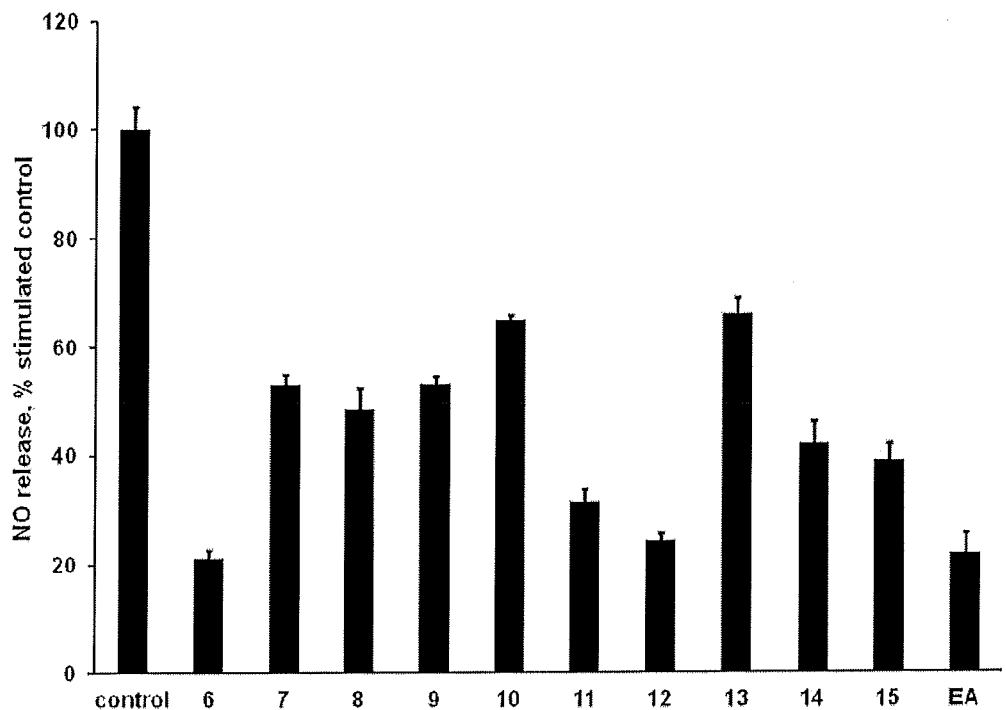
FIG. 1 shows the biological activity of conjugates 6-15. RAW264.7 cells were incubated with 30 nM of triterpenoids and 10 ng/mL IFNγ for 24 hours, and NO release was measured by the Griess reaction (EA=CDDO-ethyl amide).

Novel synthetic triterpenoids, particularly those functionalized at C-28, have now been synthesized. In particular, the synthetic triterpenoids of this invention are CDDO amino acid methyl ester derivatives having antiinflammatory and other biological properties. The synthetic triterpenoids of the invention (compounds 6-15, Table 3), were obtained by treatment of amino acid methyl esters with $Et_3N$ followed by addition of CDDO-Cl 5 in $CH_2Cl_2$ (Croft & Foley (2008) Org. Biomol. Chem. 6:1594). This procedure gave the CDDO-amino acid methyl ester conjugates in excellent yield and in highly crystalline pure form. The CDDO-Me derivatives were shown to inhibit nitric oxide production, induce the in vitro expression of heme oxygenase-1, and inhibit the proliferation of Panc-1343 pancreatic cells. Therefore, the compounds of this invention find use in the prevention or treatment of inflammation and diseases or conditions that involve immune-mediated inflammation.

In accordance with the present invention, a compound having the structure as set forth in Formula I, or a pharmaceutically acceptable salt, solvate, or enantiomer thereof is provided.

Formula I

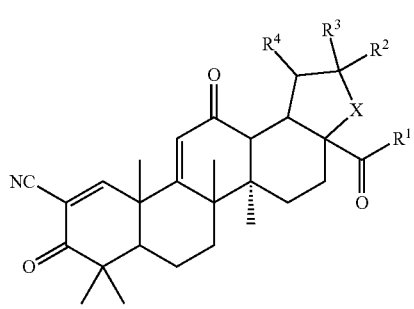

With reference to Formula I, $R^1$ is an amino acid group or amino acid derivative; $R^2$, $R^3$ and $R^4$ are each independently a hydrogen or a $C_1$-$C_3$ alkyl group; and X is —$CH_2$— or —$CH_2$—$CH_2$—.

As used herein, an amino acid group is a group having the general structure —NHCHRCOOH, where R is an organic substituent known as a "side-chain". An amino acid derivative is an amino acid group, which has a derivatized carboxylic acid group. Amino acid derivatives have the general structure —NHCHRCOOR$^5$, wherein $R^5$ is a $C_1$-$C_6$ alkyl or aryl group.

In certain embodiments, the amino acid group or amino acid derivative is, or is based upon, a natural or proteinogenic amino acid group including —NHCH(—$CH_3$)COOR$^5$ (Ala); —NHCH(—CHCH$_3$CH$_3$)COOR$^5$ (Val); —NHCH(—CH(—$CH_3$)CH$_2$CH$_3$)COOR$^5$ (Ile); —NHCH(—$CH_2$CH(—$CH_3$)$CH_3$)COOR$^5$ (Leu); —NHCH(—$CH_2$CH$_2$SCH$_3$)COOR$^5$ (Met); —NHCH(—$CH_2$Ph)COOR$^5$ (Phe); —NHCH(—$CH_2$PhOH)COOR$^5$ (Tyr); —NHCH(—$CH_2$-3-indole)COOR$^5$ (Trp); —NHCH(—$CH_2$OH)COOR$^5$ (Ser); —NHCH(—CH(—OH)CH$_3$)COOR$^5$ (Thr); —NHCH(—$CH_2$C(=O)NH$_2$)COOR$^5$ (Asn); —NHCH(—$CH_2$CH$_2$C(=O)NH$_2$)COOR$^5$ (Gln); —NHCH(—$CH_2$SH)COOR$^5$ (Phe); —NHCH(—$CH_2$CH$_2$CH$_2$NH(=NH$_2$)NH$_2$)COOR$^5$ (Arg); —NHCH(—$CH_2$-3-imidazole)COOR$^5$ (His)); NHCH(—$CH_2$CH$_2$CH$_2$CH$_2$NH$_3$)COOR$^5$ (Lys)); —NHCH(—$CH_2$CO$_2$R$^5$)COOR$^5$ (Asp); —NHCH(—$CH_2$CH$_2$CO$_2$R$^5$)COOR$^5$ (Glu); and

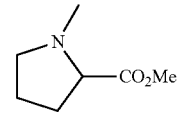

(Pro), wherein $R^5$ is a hydrogen, $C_1$-$C_6$ alkyl or aryl group.

In addition to natural amino acid groups and amino acid derivatives, the compounds of the invention can also include unnatural or non-proteinogenic amino acid groups and amino acid derivatives. Non-proteinogenic amino acid groups and amino acid derivatives include, but are not limited to, those based upon the structure of α-methylvaline, α-allylalanine, 2-aminobutyric acid, α-methylalanine or azido-alanine groups as illustrated in Table 1.

TABLE 1

| $R^1$ | Amino Acid Group |
|---|---|
| —NHCHCOOR$^5$ / \ CH$_3$ CH(—CH$_3$)CH$_3$ | α-methylvaline |
| —NHCHCOOR$^5$ / \ CH$_3$ CH$_2$CHCH$_2$ | α-allylalanine |
| —NHCHCOOR$^5$ \| CH$_2$CH$_3$ | 2-aminobutyric acid |
| —NHCHCOOR$^5$ / \ CH$_3$ CH$_3$ | 2-aminoisobutryic acid |
| —NHCHCOOR$^5$ \| CH$_2$N$_3$ | Azido-alanine |

$R^5$ is a hydrogen, $C_1$-$C_6$ alkyl or aryl group.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), or pentyl (including all isomeric forms), and the like. In some embodiments, the alkyl is substituted or unsubstituted. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy, and —C(O)O— alkyl. In certain embodiments, a $C_1$-$C_3$ alkyl group is a methyl, ethyl, propyl or isopropyl group.

"Aryl" means a monovalent or monocyclic or hydrocarbon radical of 5 to 7 ring atoms, wherein the ring is aromatic. Unless otherwise stated, the valency of the group may be located on any atom of any ring within the radical, valency rules permitting. More specifically the term aryl includes, but is not limited to, phenyl, cyclopentadienyl and the like. Unless indicated otherwise, aryl is unsubstituted or may be substituted with one or more "ring system substituents" which may be the same or different.

"Ring system substituent" means a substituent attached to an aromatic or non-aromatic ring system, which, for example, replaces an available hydrogen on the ring system. Ring system substituents may be the same or different, each being independently selected from the group of —C(=NH)(NH$_2$), —NHC(=NH)(NH$_2$), alkyl, alkenyl, alkynyl, alkoxy, acyl, alkylcarbonylamino, carboxy, carboxyalkyl, alkoxycarbonyl, alkoxycarbonylalkyl, cyano, nitro, alkylthio, halo, haloalkyl, haloalkoxy, amino, alkylamino, dialkylamino, aminocarbonyl, alkyl aminocarbonyl, dialkylaminocarbonyl, alkyl sulfonyl, cycloalkylsulfonyl, alkylsulfonylamino, alkylaminosulfonyl, haloalkylamino, oxo, hydroxy, hydroxyalkyl, hydroxyalkyloxy, hydroxyalkyloxyalkyl, alkoxyalkyloxyalkyl, aryl, heteroaryl, and the like.

In some embodiments, the compound of the invention includes an amino acid group or amino acid derivative with a simple side chain such as that found in Ala, Val, Ser and Thr. In certain embodiments, $R^5$ is a hydrogen or methyl group. In other embodiments, the compound of the invention is compound 6-15. In particular embodiments, the compound of the invention is compound 6, 11 or 12.

"Pharmaceutically acceptable salts" means salts of compounds of the present invention, which are pharmaceutically acceptable, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl) benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (Stahl & Wermuth eds., Verlag Helvetica Chimica Acta, 2002), "Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

As used herein, the term "solvate" refers to a complex of variable stoichiometry formed by a solute (in this invention, a compound of Formula I, or a salt thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid.

Processes for preparing pharmaceutically acceptable salts and solvates of the compounds of Formula I are conventional in the art. See, for example, Burger's Medicinal Chemistry and Drug Discovery, 5th Edition, Volume 1: Principles and Practice.

As used herein, the term "enantiomer" denotes a compound having a center of chirality and being one of two stereoisomers that are non-superposable complete mirror images of each other. As known in the art, enantiomers differ from each other in their ability to rotate plane-polarized light and may be classified according to the CIP (Cahn-Ingold-Prelog)-convention as S- or R-enantiomer. The S- and R-configurations represent the three-dimensional orientation of the four substituents about the chiral center carbon atom.

In certain embodiments, the compound is provided as predominantly one enantiomer. The phrase "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer. "Diastereomers" are stereoisomers of a given compound that are not enantiomers.

Compounds of Formula I can be prepared from oleanolic acid, ursolic acid or betulinic acid, and purified using any suitable methodology routinely practiced in the art (see, e.g., Example 1).

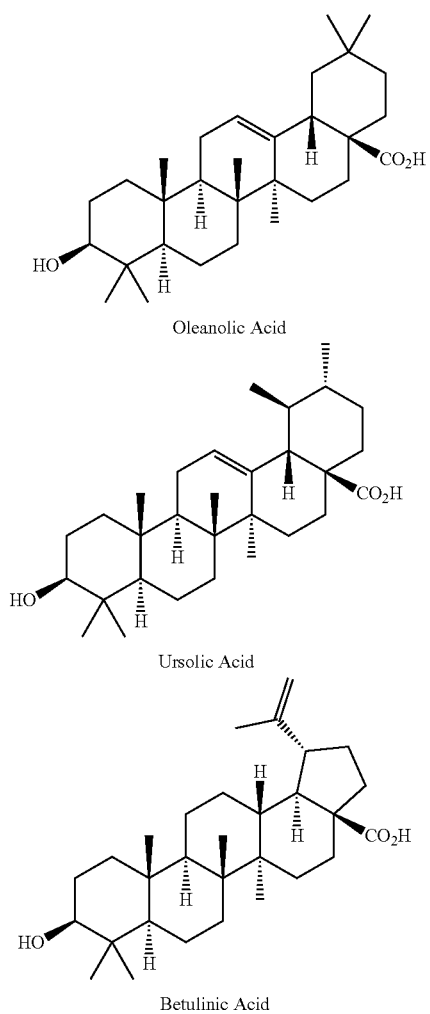

Oleanolic Acid

Ursolic Acid

Betulinic Acid

Furthermore, the compounds of the invention can be analyzed for their pharmacological properties by routine methodologies. For example, kinetic solubility can be measured using a direct UV absorbance method or thermodynamic solubility can be measured. In addition, stability in gastrointestinal fluids can be determined by conventional methods (Asafu-Adjaye, et al. (2007) *J. Pharm. Biomed. Anal.* 43:1854-1859), e.g., 1 hour in simulated gastric fluid (pH 1.2, pepsin) at 37° C. and/or 3 hours in simulated intestinal fluid (pH 6.8, pancreatin). Furthermore, using the Parallel Artificial Membrane Permeability Assay (PAMPA)-blood-brain barrier (BBB) permeability assay (Di, et al. (2009) *J. Pharm. Sci.* 98:1980-1991) or B-P dialysis (Kalvass & Maurer (2002) *Biopharm. Drug Dispos.* 23(8):327-38), brain penetration can be assessed. Furthermore, lipophilicity can be estimated by partitioning between octanol and water using a shake flask method or pH metric method and permeability can be assessed using the Caco-2 cell layer method of PAMPA assay.

In general, CDDO is the prototype for a large number of compounds in a family of agents that have been shown useful in a variety of contexts. For example, CDDO-Me and CDDO-Im are reported to possess the ability to modulate transforming growth factor-β (TGF-β)/Smad signaling in several types of cells (Suh, et al. (2003) *Cancer Res.* 63:1371-1376; Minns, et al. (2004) *Gastroenterology* 127:119-126; Mix, et al. (2004) *Mol. Pharmacol.* 65:309-318). Both are known to be potent inducers of heme-oxygenase-1 and Nrf2/ARE signaling (Liby, et al. (2005) *Cancer Res.* 65:4789-4798), and a series of synthetic triterpenoid analogs of oleanolic acid have also been shown to be potent inducers of the phase 2 response, that is elevation of NAD(P)H-quinone oxidoreductase and heme oxygenase 1 (HO-1), which is a major protector of cells against oxidative and electrophile stress (Dinkova-Kostova, et al. (2005) *Proc. Natl. Acad. Sci. USA* 102:4584-4589). Like previously identified phase 2 inducers, the synthetic triterpenoid analogs were shown to use the antioxidant response element-Nrf2-Keap1 signaling pathway.

CDDO-methyl ester 3 (bardoxolone methyl) is an Antioxidant Inflammation Modulator (AIM) in clinical development for inflammation and cancer-related indications that inhibits immune-mediated inflammation by restoring redox homeostasis in inflamed tissues. It induces the cytoprotective transcription factor Nrf2 and suppresses the activities of the pro-oxidant and pro-inflammatory transcription factors NF-κB and STAT3. Further, synthetic triterpenoids such as CDDO, CDDO-Im, CDDO-Me, CDDO-EA, CDDO-MA and CDDO-TFEA have been shown to inhibit the proliferation and/or induce apoptosis of cancer cells including, but not limited to, B and T cell leukemias (AML, APL, CML, Sezary syndrome), lymphomas/mycosis fungoides and plasmacytomas, ER-positive and -negative breast cancer, ovarian cancer, prostate cancer, non-small cell lung carcinoma, pancreatic cancer, colon cancer, osteosarcoma, chondrosarcoma, liposarcoma, Ewing's sarcoma, chordoma, multiple myeloma, melanoma and other skin cancers, glioblastoma and neuroblastoma. See Liby & Sporn (2012) *Pharmacol. Rev.* 64:972-1003. Accordingly, in certain embodiments, the compounds of this invention are also of use in the prevention or treatment of cancer. Indeed, it is expected that conjugation of CDDO with amino acid methyl esters can enhance the activity and selectivity of antitumor drugs.

At slightly higher concentrations than those required to inhibit inflammation and induce Nrf2, synthetic triterpenoids such as CDDO, CDDO-Im, CDDO-Me, and CDDO-EA, have been shown to induce differentiation of a variety of primary leukemic blasts or human leukemia cell lines, in addition to neuronal differentiation of PC12 cells, adipocytic differentiation of 3T3L1 fibroblasts, osteoblastic differentiation of Saos-2 osteosarcoma cells, megakaryocytic differentiation of normal hemopoietic progenitor cells and chondrogenic differentiation of human bone marrow-derived mesenchymal stem cells. See Suh, et al. (1999) *Cancer Res.* 59:336-341; Suh, et al. (2012) *Osteoarthritis Cartilage* 20:446-450; Konopleva, et al. (2002) *Blood* 99:326-335; Ito, et al. (2001) *Mol. Pharmacol.* 59:1094-1099; and Petronelli, et al. (2011) *Leuk. Res.* 35:534-44. Thus, the compounds of this invention are also of use in facilitating the differentiation of a stem or progenitor cell.

In vivo, CDDO-methyl ester 3 has demonstrated significant single agent anti-inflammatory activity in several animal models of inflammation such as renal damage in the cisplatin model and acute renal injury in the ischemia-reperfusion model. In addition, significant reductions in serum creatinine have been observed in patients treated with CDDO-methyl ester 3. Thus, in one aspect of the invention, the compounds of the present invention are used for treating a subject having a renal disease or condition caused by elevated levels of oxidative stress in one or more tissues. The oxidative stress may be accompanied by either acute or chronic inflammation. The oxidative stress may be caused by acute exposure to an external agent such as ionizing radiation or a cytotoxic chemotherapy agent (e.g., doxorubicin), by trauma or other acute tissue injury, by ischemia/reperfusion injury, by poor circulation or anemia, by localized or systemic hypoxia or hyperoxia, or by other abnormal physiological states such as hyperglycemia or hypoglycemia.

Activation of the Nrf2/ARE pathway by synthetic triterpenoids is also of use in protecting against a number of diseases driven by inflammatory and oxidative stress. Indeed, as summarized in Table 2, triterpenoids are effective in a wide variety of preclinical disease models in all of the major organs that have been tested, including the brain, eye, lung, heart, liver, and kidney. The synthetic triterpenoids also provide protection against radiation and chemical insults and help regulate the immune system and metabolism.

TABLE 2

| Organ | Preclinical Disease Model |
| --- | --- |
| Brain | Alzheimer's Disease, Parkinson's Disease, Huntington's Disease, Amyotrophic lateral sclerosis |
| Eye | Light damage, uveitis, ischemica/reperfusion injury, corneal scarring |
| Lung | Chronic obstructive pulmonary disease, acute lung injury or acute respiratory distress syndrome, emphysema/asthma, fibrosis |
| Heart | Cardiomyopathy induced by smoking |
| Liver | Hepatotoxicity from aflatoxin, ConA, or acetaminophen |
| Kidney | Nephrotoxicity from ischemia-reperfusion injury and cisplatin |

See, Liby & Sporn (2012) supra.

As indicated, activation of the Nrf2 pathway is also useful for maintaining homeostasis in the cardiovascular system. Oxidative stress is a primary contributor to the development and progression of cardiovascular diseases (Li, et al. (2009) *Expert Opin. Ther. Targets* 13:785-794; Koenitzer & Freeman (2010) *Ann. Rev. Acad. Sci.* 1203:45-52), but the synthetic triterpenoids eliminate the damage of ROS in various models of cardiomyopathy. Dihydro CDDO-TFEA, in which the double bond in the C ring is removed, binds to Keap1, allowing Nrf2 translocation to the nucleus and transcription of Nrf2 target genes in cardiomyocytes in vitro and in vivo. The reduction by this synthetic triterpenoid in the production of ROS/reactive nitrogen species, which is induced by angiotensin II activation of NADPH oxidase, in these cells is eliminated with knockdown of Nrf2 (Ichikawa, et al. (2009) *PLoS One* 4:e8391). Moreover, by inducing expression of HO-1, CDDO-Im increases the availability of NO and decreases levels of ROS and endothelial NOS in naive or stressed endothelial cells, thus mediating endothelial NOS coupling and vascular homeostasis (Heiss, et al. (2009) *J. Biol. Chem.* 284:31579-31586). Although cigarette smoking triggers cardiac dysfunction in the right ventricle that is worse in $Nrf2^{-/-}$ mice than in $Nrf2^{-/-}$ mice, CDDO-Im prevents the cardiac damage from smoking. Changes to end-systolic pressure, ejection fraction, and isovolumetric relaxation time after 6 months of cigarette smoke are eliminated in mice when CDDO-Im is administered concurrently with cigarette smoke, but the cardioprotective effects of CDDO-Im in this model are mostly absent in $Nrf2^{-/-}$ mice (Sussan, et al. (2009) *Proc. Natl. Acad. Sci. USA* 106:250-255).

Synthetic triterpenoids are also beneficial in animal studies of obesity and diabetes. Nrf2 can bind to an ARE on the promoter of the aryl hydrocarbon receptor, which then inhibits adipocyte differentiation. By activating Nrf2, CDDO-Im has been shown to induce Ahr transcription and block lipid accumulation in $Nrf2^{-/-}$ mouse embryonic fibroblasts (MEFs) but not in $Nrf2^{-/-}$ MEFs in vitro (Shin, et al. (2007) *Mol. Cell Biol.* 27:7188-7197). When given orally to mice, CDDO-Im reduces the weight gain, adipose levels, and lipid accumulation in the liver that accompany a highfat diet but has no effect on weight gain or energy balance in mice fed a normal diet. The reduction in obesity in the group treated with CDDO-Im is accompanied by increased energy expenditure and down-regulation of pathways regulating fatty acid synthesis in the liver, but these effects are lost in Nrf2-deficient mice (Shin, et al. (2009) *J. Pharmacol.* 620:138-144). In mice fed a high-fat diet or in mice with a defective leptin receptor (Leprdb/db), CDDO-Me not only improved glucose tolerance and insulin sensitivity but also lowered levels of free fatty acids and plasma triglycerides. Although CDDO-Me reduced total body fat and suppressed production of the proinflammatory cytokines IL-1, IL-6, and TNFα in mice fed a high-fat diet, the antidiabetic effects of this synthetic triterpenoid may be mediated by stimulating phosphorylation of LKB1 and AMPK in muscle and liver, as knockdown of AMPK reduces glucose uptake in cells treated with CDDO-Me (Saha, et al. (2010) *J. Biol. Chem.* 285:40581-40592).

As synthetic triterpenoids exhibiting activity comparable to or better than that of, e.g., CDDO-Me and CDDO-EA, the CCDO amino acid methyl ester conjugates of this invention find application in methods for the prevention or treatment of one or more of the above-references diseases or conditions. Such methods include administering to a subject a therapeutically effective amount of a compound of this invention, such as those described above or throughout this specification. Treatment may be administered preventively in advance of any signs or symptoms of the disease or condition, or it may be administered therapeutically in settings involving established oxidative stress and inflammation.

As used herein, the term "subject" or "patient" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Prevention" or "preventing" includes inhibiting the onset of a disease in a subject or patient which may be at risk and/or predisposed to the disease but does not yet experience or display any or all of the pathology or symptomatology of the disease, and/or slowing the onset of the pathology or symptomatology of a disease in a subject or patient which may be at risk and/or predisposed to the disease but does not yet experience or display any or all of the pathology or symptomatology of the disease.

"Treatment" or "treating" includes inhibiting a disease in a subject or patient experiencing or displaying the pathology or symptomatology of the disease (e.g., arresting further development of the pathology and/or symptomatology), ameliorating a disease in a subject or patient that is experiencing or displaying the pathology or symptomatology of the disease (e.g., reversing the pathology and/or symptomatology), and/or effecting any measurable decrease in a disease in a subject or patient that is experiencing or displaying the pathology or symptomatology of the disease.

"Therapeutically effective amount" or "pharmaceutically effective amount" means that amount which, when administered to a subject or patient for treating a disease, is sufficient to effect such treatment for the disease.

Given their biological properties, the compounds of this invention can provide protective effects against oxidative stress and inflammation, and are therefore particularly useful in the treatment and/or prevention of diseases, such as renal/kidney disease (RKD) including both acute and chronic indications, insulin resistance, diabetes, cancer, endothelial dysfunction, fatty liver disease, cardiovascular disease (CVD), and related disorders. Although the unifying factors are not completely understood, dysfunction of the vascular endothelium has been implicated as a significant pathological factor in systemic cardiovascular disease, chronic kidney disease, and diabetes. Acute or chronic oxidative stress in vascular endothelial cells has been implicated in the development of endothelial dysfunction, and is strongly associated with chronic inflammatory processes. Therefore, an agent capable of relieving oxidative stress and concomitant inflammation in the vascular endothelium may alleviate dysfunction and restore endothelial homeostasis. Currently, combination therapy is typically required in patients to achieve improvements in measures of glycemic control and cardiovascular disease, including the use of angiotensin-converting enzyme inhibitors or angiotensin II receptor blockers to alleviate hypertension and slow the progression of chronic kidney disease. By achieving simultaneous and clinically meaningful improvements in all of these parameters, especially measures of renal function, compounds of the invention can provide a significant improvement over currently available therapies. In some aspects, the compounds of the present invention may be used to treat a combination of the above conditions as a single therapy, or in combination with fewer additional therapies than would currently be used.

Administration of the compounds of the present invention to a patient will follow general protocols for the administration of pharmaceuticals, taking into account the toxicity, if any, of the drug. It is expected that the treatment cycles would be repeated as necessary.

The compounds of the present invention may be administered by a variety of methods, e.g., orally or by injection (e.g. subcutaneous, intravenous, intraperitoneal, etc.). Depending on the route of administration, the active compounds may be coated by a material to protect the compound from the action of acids and other natural conditions which may inactivate the compound. They may also be administered by continuous perfusion/infusion of a disease or wound site. Specific examples of formulations, including a polymer-based dispersion of CDDO-Me that showed improved oral bioavailability, are provided in U.S. application Ser. No. 12/191,176. It will be recognized by those skilled in the art that other methods of manufacture may be used to produce dispersions of the present invention with equivalent properties and utility. Such alternative methods include but are not limited to solvent evaporation, extrusion, such as hot melt extrusion, and other techniques.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The therapeutic compound may also be administered parenterally, intraperitoneally, intraspinally, or intracerebrally. Dispersions may be prepared in, e.g., glycerol, liquid polyethylene glycols, mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier may be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

The actual dosage amount of a compound of the present invention or composition comprising a compound of the present invention administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

In some embodiments, the pharmaceutically effective amount is a daily dose from about 0.1 mg to about 500 mg of the compound. In some variations, the daily dose is from about 1 mg to about 300 mg of the compound. In some variations, the daily dose is from about 10 mg to about 200 mg of the compound. In some variations, the daily dose is about 25 mg of the compound. In other variations, the daily dose is about 75 mg of the compound. In still other variations, the daily dose is about 150 mg of the compound. In further variations, the daily dose is from about 0.1 mg to about 30 mg of the compound. In some variations, the daily dose is from about 0.5 mg to about 20 mg of the compound. In some variations, the daily dose is from about 1 mg to about 15 mg of the compound. In some variations, the daily dose is from about 1 mg to about 10 mg of the compound. In some variations, the daily dose is from about 1 mg to about 5 mg of the compound.

In some embodiments, the pharmaceutically effective amount is a daily dose is 0.01-25 mg of compound per kg of body weight. In some variations, the daily dose is 0.05-20 mg of compound per kg of body weight. In some variations, the daily dose is 0.1-10 mg of compound per kg of body weight. In some variations, the daily dose is 0.1-5 mg of compound per kg of body weight. In some variations, the daily dose is 0.1-2.5 mg of compound per kg of body weight.

In some embodiments, the pharmaceutically effective amount is a daily dose is of 0.1-1000 mg of compound per kg of body weight. In some variations, the daily dose is 0.15-20 mg of compound per kg of body weight. In some variations, the daily dose is 0.20-10 mg of compound per kg of body weight. In some variations, the daily dose is 0.40-3 mg of compound per kg of body weight. In some variations, the daily dose is 0.50-9 mg of compound per kg of body weight. In some variations, the daily dose is 0.60-8 mg of compound per kg of body weight. In some variations, the daily dose is 0.70-7 mg of compound per kg of body weight. In some variations, the daily dose is 0.80-6 mg of compound per kg of body weight. In some variations, the daily dose is 0.90-5 mg of compound per kg of body weight. In some variations, the daily dose is from about 1 mg to about 5 mg of compound per kg of body weight.

An effective amount typically will vary from about 0.001 mg/kg to about 1,000 mg/kg, from about 0.01 mg/kg to about 750 mg/kg, from about 0.1 mg/kg to about 500 mg/kg, from about 0.2 mg/kg to about 250 mg/kg, from about 0.3 mg/kg to about 150 mg/kg, from about 0.3 mg/kg to about 100 mg/kg, from about 0.4 mg/kg to about 75 mg/kg, from about 0.5 mg/kg to about 50 mg/kg, from about 0.6 mg/kg to about 30 mg/kg, from about 0.7 mg/kg to about 25 mg/kg, from about 0.8 mg/kg to about 15 mg/kg, from about 0.9 mg/kg to about 10 mg/kg, from about 1 mg/kg to about 5 mg/kg, from about 100 mg/kg to about 500 mg/kg, from about 1.0 mg/kg to about 250 mg/kg, or from about 10.0 mg/kg to about 150 mg/kg, in one or more dose administrations daily, for one or several days (depending, of course, of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some particular embodiments, the amount is less than 10,000 mg per day with a range, for example, of 750 mg to 9,000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day, less than 10 mg/kg/day, or less than 5 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is within ±10% of the blood glucose level of a non-diabetic subject.

In other non-limiting examples, a dose may also include from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 1 mg/kg/body weight to about 5 mg/kg/body weight, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present invention may comprise, for example, at least about 0.1% of a compound of the present invention. In other embodiments, the compound of the present invention may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

Non-limiting specific formulations include polymer dispersions (see U.S. application Ser. No. 12/191,176). Some of the formulations reported therein exhibited higher bioavailability than either the micronized Form A or nanocrystalline Form A formulations. Additionally, the polymer dispersion based formulations demonstrated further surprising improvements in oral bioavailability relative to the micronized Form B formulations. For example, the methacrylic acid copolymer, Type C and HPMC-P formulations showed the greatest bioavailability in the subject monkeys.

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

It is contemplated that other anti-inflammatory agents may be used in conjunction with the treatments of the current invention. For example, other COX inhibitors may be used, including arylcarboxylic acids (salicylic acid, acetylsalicylic acid, diflunisal, choline magnesium trisalicylate, salicylate, benorylate, flufenamic acid, mefenamic acid, meclofenamic acid and triflumic acid), arylalkanoic acids (diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin and sulindac) and enolic acids (phenylbutazone, oxyphenbutazone, azapropazone, feprazone, piroxicam, and isoxicam. See also U.S. Pat. No. 6,025,395, which is incorporated herein by reference.

Dietary and nutritional supplements with reported benefits for treatment or prevention of Parkinson's, Alzheimer's, multiple sclerosis, amyotrophic lateral sclerosis, rheumatoid arthritis, inflammatory bowel disease, and all other diseases whose pathogenesis is believed to involve excessive production of either nitric oxide (NO) or prostaglandins, such as acetyl-L-carnitine, octacosanol, evening primrose oil, vitamin B6, tyrosine, phenylalanine, vitamin C, L-dopa, or a combination of several antioxidants may be used in conjunction with the compounds of the current invention.

Other particular secondary therapies include immunosuppressants (for transplants and autoimmune-related RKD), anti-hypertensive drugs (for high blood pressure-related RKD, e.g., angiotensin-converting enzyme inhibitors and angiotensin receptor blockers), insulin (for diabetic RKD), lipid/cholesterol-lowering agents (e.g., HMG-CoA reductase inhibitors such as atorvastatin or simvastatin), treatments for hyperphosphatemia or hyperparathyroidism associated with CKD (e.g., sevelamer acetate, cinacalcet), dialysis, and dietary restrictions (e.g., protein, salt, fluid, potassium, phosphorus).

The invention is described in greater detail by the following non-limiting examples.

EXAMPLE 1

Preparation of CDDO Amino Acid Methyl Ester Derivatives

The amino acid methyl ester hydrochloride (1.2 mmol) was dissolved in 10 mL of $CH_2Cl_2$ and treated with 5 equiv of $Et_3N$ at ice bath temperature (Table 3). The acid chloride 5 (1 mmol) in $CH_2Cl_2$ was added dropwise and the reaction mixture was stirred at room temperature until thin layer chromatography analysis showed complete consumption of 5. The reaction was then washed in turn with 1 N hydrochloric acid, water, and saturated sodium chloride solution. The organic layer was dried over $MgSO_4$ and then concentrated in vacuo. The crude was purified on silica gel column to afford 6-15 in 78-90% yield.

TABLE 3

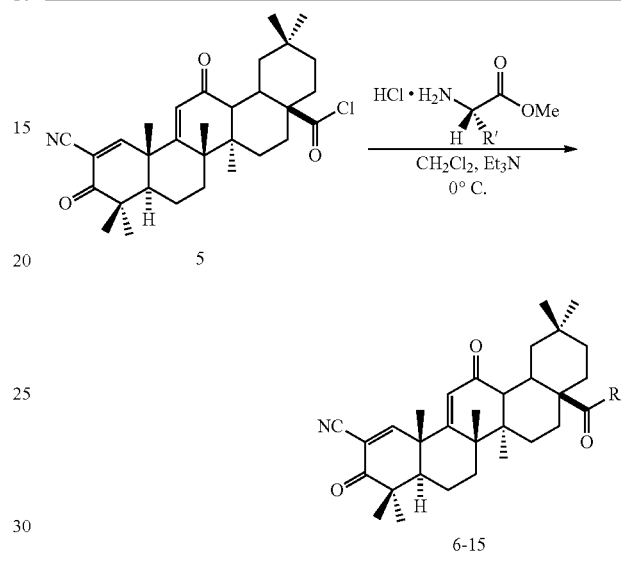

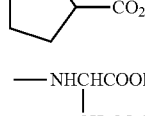

| R | | % Yield | Compound |
|---|---|---|---|
| —NHCHCOOMe<br>\|<br>$CH_3$ | (Ala) | 88 | 6 |
| —NHCHCOOMe<br>\|<br>$CH_2CH(CH_3)_2$ | (Leu) | 90 | 7 |
| (pyrrolidine-CO₂Me) | (Pro) | 80 | 8 |
| —NHCHCOOMe<br>\|<br>$CH_2CO_2Me$ | (Asp) | 90 | 9 |
| —NHCHCOOMe<br>\|<br>$CH_2Ph$ | (Phe) | 87 | 10 |
| —NHCHCOOMe<br>\|<br>$CH(CH_3)_2$ | (Val) | 89 | 11 |
| —NHCHCOOMe<br>\|<br>$CH_2OH$ | (Ser) | 81 | 12 |
| —NHCHCOOMe<br>\|<br>$CH_2PhOH$ | (Tyr) | 78 | 13 |
| —NHCHCOOMe<br>\|<br>$CH_2$(3-indole) | (Trp) | 79 | 14 |

TABLE 3-continued

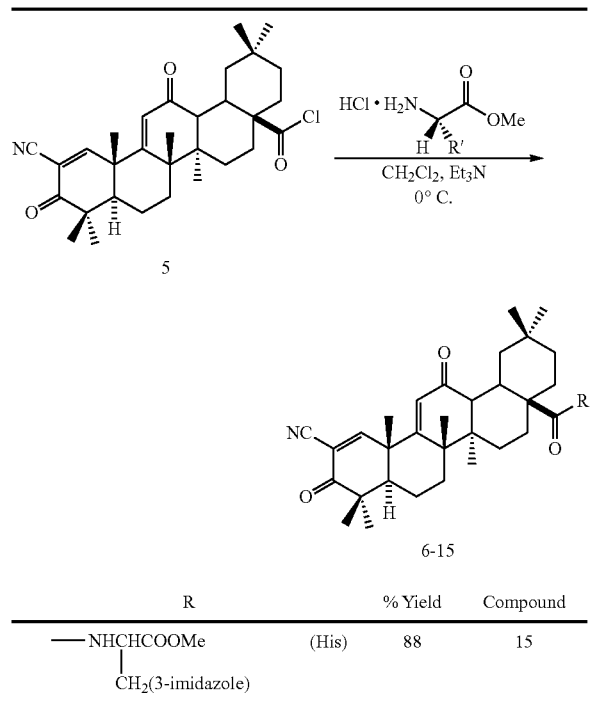

| R | % Yield | Compound |
|---|---|---|
| —NHCHCOOMe<br>   \|<br>   CH$_2$(3-imidazole) | (His) 88 | 15 |

Free amino acid derivatives of the amino acid methyl esters of this invention can be readily prepared by mild ester hydrolysis.

EXAMPLE 2

Activity of CDDO Amino Acid Methyl Ester Derivatives

Since oxidative and inflammatory stress contribute to the pathogenesis of numerous chronic diseases, the inhibition of the pro-inflammatory mediator, nitric oxide (NO), was used as a primary screen of the CDDO amino acid methyl ester derivatives (Barnes & Liew (1995) *Immunol. Today* 16:128; Qureshi, et al. (2011) *Lipids Health Dis.* 10:177). The RAW264.7 cell line (American Type Culture Collection, Manassas, Va.) was maintained in DMEM containing 10% fetal bovine serum (Invitrogen, Carlsbad, Calif.). RAW264.7 cells (5×10$^5$ cells per well) were plated in 96-well plates. The following day, the cells were incubated with 30 nM of triterpenoids and 10 ng/ml IFNγ (R & D Systems) for 24 hours. NO was measured as nitrite by the Griess reaction. The inhibition of NO by various amino acid methyl ester conjugates of CDDO in RAW264.7 cells stimulated with IFNγ, is shown in FIG. 1. The three most active compounds were 6, 11 and 12. The activity of these compounds was comparable to CDDO-ethyl amide (CDDO-EA) (Liby & Sporn (2012) supra). In contrast, the incorporation of amino acids with more complex side chains reduced the activity as seen in compounds 7-10 and 13-15.

As synthetic triterpenoids are known to act through the Nrf2 pathway to induce anti-inflammatory and cytoprotective genes (Liby & Sporn (2012) supra), additional assays were performed for the three most active compounds: 6, 11 and 12. Specifically, the compounds were assessed for their ability to induce the in vitro expression of heme oxygenase-1 (HO-1), an important anti-inflammatory enzyme, in RAW cells after 6 hours of treatment. This analysis indicated that these compounds were all potent inducers of HO-1 at 30 and 300 nM concentrations, wherein compound 6 was more active than compounds 11 and 12 and was equipotent to CDDO-EA.

Figure 2:
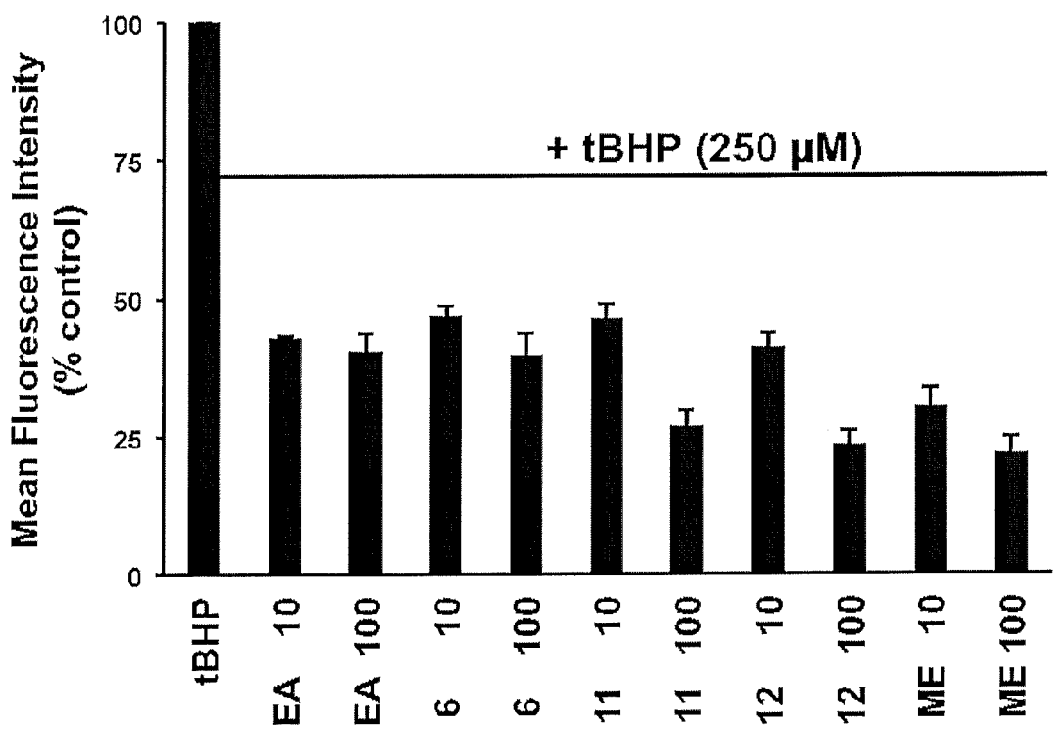
FIG. 2 shows that the triterpenoids of the invention reduce reactive oxygen species (ROS) levels. RAW264.7 cells were incubated with 10 and 100 nM of the synthetic triterpenoids for 18 hours, $H_2DCFA$ was then added for 30 minutes and the cells were challenged with 250 µM of tert-butyl hydroperoxide for 15 minutes to induce ROS. Mean fluorescence intensity of 50,000 cells was detected by flow cytometry. The results were obtained from three independent experiments.

The antioxidative activity of these compounds was explored as well. This experiment was based on the deacetylation and then oxidation of the non-fluorescent reagent 2',7'-dichlorodihydrofluorescein diacetate (H$_2$DCFA) to a fluorescent derivative. To study the effects of the TPs on oxidative stress, RAW cells were treated with 10-100 nM of the TPs for 18 hours. Cells were then incubated with 10 μM H$_2$DCFA for 2 hours and challenged with 250 μM of tert-butyl hydroperoxide (tBHP) for 15 minutes. The mean fluorescence intensity was measured by flow cytometry, using a 480 nm excitation wavelength and a 525 nm emission wavelength. As shown in FIG. 2, the three compounds were found to block the production of reactive oxygen species in tBHP-exposed cells, with an inhibition of better than 50% at the lowest concentration of 10 nM. The protection was slightly better at 100 nM for compounds 11, 12 and CDDO-Me.

Figure 3:
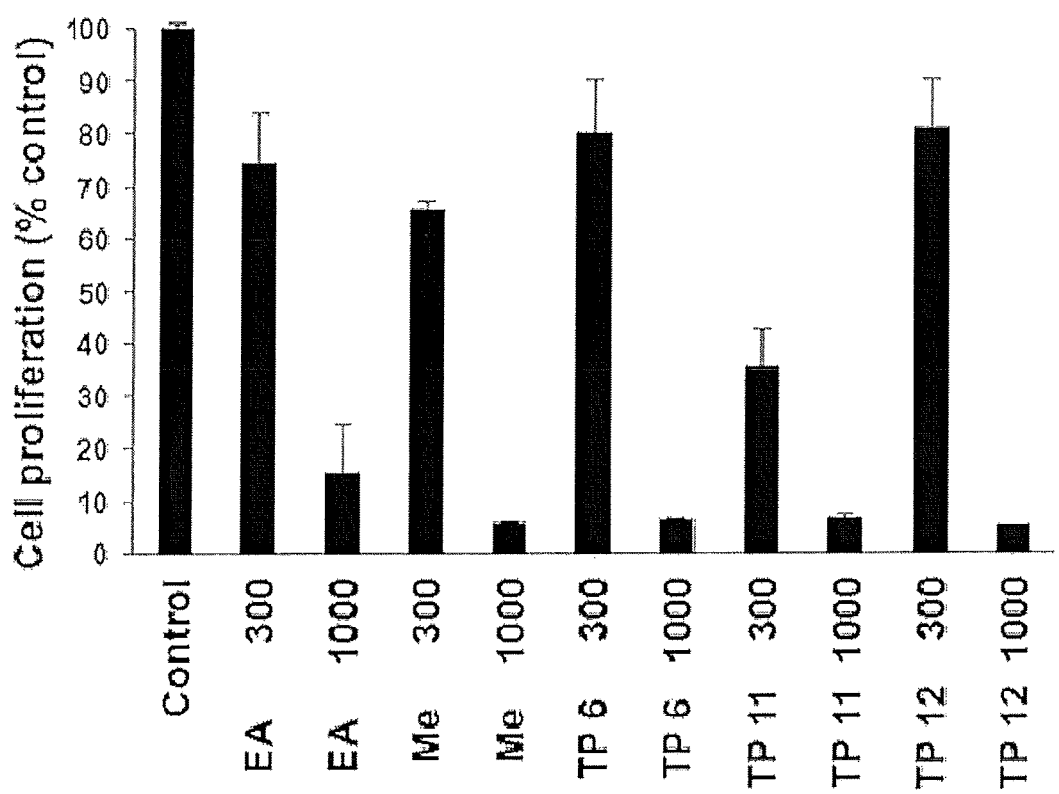
FIG. 3 shows that the triterpenoids of the invention inhibit the proliferation of pancreatic cancer cells. Panc-1343 cells were seeded at a density of $2.5 \times 10^3$ cells/well in 96-well plates and cultured overnight. Cells were treated on the next day with 0.3-1 µM of the triterpenoids and then assayed for antiproliferative activity after 72 hours of incubation, using MTT. Data were obtained from three independent experiments.

Because CDDO-EA and CDDO-Me are reported to have antiproliferative activity against cancer cell lines, compounds 6, 11 and 12 were tested in the MTT (3-(4,5-dimethylthiazol-2-yl)-2,5-diphenyl-tetrazolium bromide) assay. Panc-1343 cells (derived from a pancreatic tumor of the KPC mouse model) were treated with 300 nM and 1000 nM of the drugs for 72 hours. The three compounds appeared to be as potent as the parent molecules in inhibiting the proliferation of the pancreatic cells (FIG. 3). When treated with 1 μM of the TP, less than 10% of the cancer cells were viable after 72 hours.

This analysis demonstrated that modification of the C28 carboxylic acid as amino acid methyl ester conjugates yielded a number of derivatives with biological activities comparable to known oleanane triterpenoids.

What is claimed is:

1. A compound of Formula I, or a pharmaceutically acceptable salt, solvate, or enantiomer thereof:

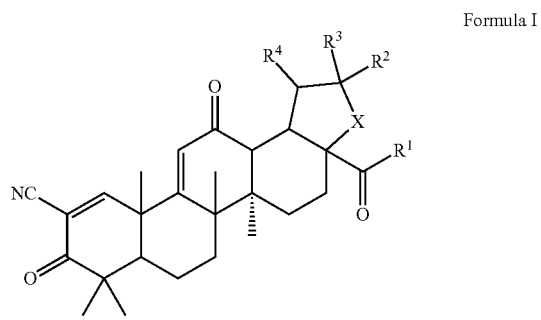

Formula I wherein R$^1$ is an amino acid group or amino acid derivative; R$^2$, R$^3$ and R$^4$ are each independently a hydrogen or a C$_1$-C$_3$ alkyl group; and X is —CH$_2$— or —CH$_2$—CH$_2$—.

2. The compound of claim 1, wherein the amino acid group or amino acid derivative comprises —NHCH(—CH$_3$)COOR$^5$; —NHCH(—CHCH$_3$CH$_3$)COOR$^5$; —NHCH(—CH(—CH$_3$) CH$_2$CH$_3$)COOR$^5$; —NHCH(—CH$_2$CH(—CH$_3$)CH$_3$)COOR$^5$; —NHCH(—CH$_2$CH$_2$SCH$_3$)COOR$^5$; —NHCH(—CH$_2$Ph)COOR$^5$; —NHCH(—CH$_2$PhOH) COOR$^5$; —NHCH(—CH$_2$-3-indole)COOR$^5$; —NHCH(—CH$_2$OH)COOR$^5$; —NHCH(—CH(—OH) CH$_3$)COOR$^5$; —NHCH(—CH$_2$C(=O) NH$_2$)COOR$^5$; —NHCH(—

$CH_2CH_2C(=O)NH_2)COOR^5$; —NHCH(—$CH_2SH$)COOR$^5$; —NHCH(—$CH_2CH_2CH_2NH(=NH_2)NH_2$)COOR$^5$; —NHCH(—$CH_2$-3-imidazole)COOR$^5$; NHCH(—$CH_2CH_2CH_2CH_2NH_3$)COOR$^5$; —NHCH(—$CH_2CO_2R^5$)COOR$^5$; —NHCH(—$CH_2CH_2CO_2R^5$)COOR$^5$; or

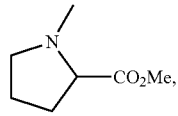

wherein R$^5$ is a hydrogen, $C_1$-$C_6$ alkyl or aryl group.

3. The compound of claim 1, wherein the amino acid group or amino acid derivative comprises:

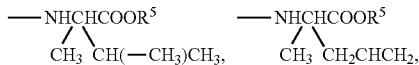

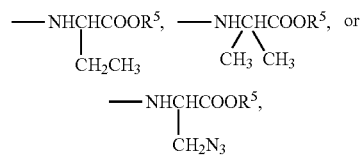

wherein R$^5$ is a hydrogen, $C_1$-$C_6$ alkyl or aryl group.

4. A pharmaceutical composition comprising the compound of claim 1 in admixture with a pharmaceutically acceptable carrier.

5. A method for treating inflammation or a disease or condition mediated by inflammation comprising administering the pharmaceutical composition of claim 4 to a subject in need of treatment thereby treating the subject's inflammation or disease or condition mediated by inflammation.

* * * * *